(12) United States Patent
Murakami

(10) Patent No.: US 8,902,304 B2
(45) Date of Patent: Dec. 2, 2014

(54) ENDOSCOPE SYSTEM

(75) Inventor: Hiroshi Murakami, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 545 days.

(21) Appl. No.: 13/113,042

(22) Filed: May 21, 2011

(65) Prior Publication Data
US 2011/0298908 A1 Dec. 8, 2011

(30) Foreign Application Priority Data
Jun. 7, 2010 (JP) ................................ P2010-130220

(51) Int. Cl.

| | | |
|---|---|---|
| A62B 1/04 | (2006.01) | |
| H04N 7/01 | (2006.01) | |
| G06K 9/40 | (2006.01) | |
| A61B 1/00 | (2006.01) | |
| H04L 25/49 | (2006.01) | |
| H04N 5/353 | (2011.01) | |
| A61B 1/05 | (2006.01) | |
| H04N 5/343 | (2011.01) | |
| A61B 18/14 | (2006.01) | |
| A61B 1/005 | (2006.01) | |
| H04N 5/225 | (2006.01) | |
| A61B 1/018 | (2006.01) | |

(52) U.S. Cl.
CPC ........ *H04L 25/4908* (2013.01); *A61B 1/00009* (2013.01); *A61B 18/1492* (2013.01); *A61B 1/0052* (2013.01); *H04N 2005/2255* (2013.01); *A61B 1/00039* (2013.01); *A61B 2018/1475* (2013.01); *H04N 5/3532* (2013.01); *A61B 1/00018* (2013.01); *A61B 1/00045* (2013.01); *A61B 1/0051* (2013.01); *A61B 1/05* (2013.01); *A61B 1/018* (2013.01); *H04N 5/343* (2013.01)
USPC .............................. 348/65; 348/448; 382/254

(58) Field of Classification Search
None
See application file for complete search history.

(56) References Cited

U.S. PATENT DOCUMENTS 4,473,841 A * 9/1984 Murakoshi et al. ............. 348/65
2001/0022612 A1 9/2001 Higuchi et al.
(Continued)

FOREIGN PATENT DOCUMENTS

DE 102009018255 A1 10/2009
EP 2096865 A2 9/2009
(Continued)

OTHER PUBLICATIONS

European Search Report dated Sep. 26, 2011.
(Continued)

*Primary Examiner* — Joseph Ustaris
*Assistant Examiner* — Frederick Bailey
(74) *Attorney, Agent, or Firm* — McGinn IP Law Group, PLLC

(57) ABSTRACT

An endoscope system includes an endoscope including an imaging part and a controller separated from the endoscope and connected to the endoscope through a signal line. The imaging part includes a plurality of light receiving portions two-dimensionally arranged and a driving part that reads a charge signal stored in each of the light receiving portions. The driving part conducts read scan in which read of the charge signals from the light receiving portions in a main and sub scanning direction. The driving part changes an order of outputting the lines in the image data by conducting the read scan on all lines included in the captured image so as to scan some lines successively with a prescribed number of lines interlaced along the sub scanning direction and scan the other lines successively from an interlaced line with the prescribed number of lines interlaced.

11 Claims, 13 Drawing Sheets

(56) References Cited

U.S. PATENT DOCUMENTS

| | | | |
|---|---|---|---|
| 2002/0063869 A1* | 5/2002 | Matsumura | 358/1.2 |
| 2003/0218680 A1* | 11/2003 | Shiohara | 348/308 |
| 2004/0239802 A1* | 12/2004 | Kim et al. | 348/448 |
| 2006/0005096 A1* | 1/2006 | Cullen et al. | 714/742 |
| 2006/0050143 A1* | 3/2006 | Ouchi | 348/65 |
| 2006/0098888 A1* | 5/2006 | Morishita | 382/254 |
| 2007/0159554 A1* | 7/2007 | Tomizawa et al. | 348/448 |
| 2007/0286009 A1* | 12/2007 | Norman | 365/230.03 |
| 2008/0100701 A1 | 5/2008 | Tannai | |
| 2008/0136903 A1* | 6/2008 | Takada et al. | 348/65 |
| 2009/0213212 A1* | 8/2009 | Nakamura | 348/65 |
| 2009/0225219 A1 | 9/2009 | Abe | |
| 2010/0097453 A1* | 4/2010 | Endo et al. | 348/65 |

FOREIGN PATENT DOCUMENTS

| | | |
|---|---|---|
| JP | 60-55923 A | 4/1985 |
| JP | 2002-209838 A | 7/2002 |
| JP | 2008-080007 A | 4/2008 |
| JP | 2008-110004 A | 5/2008 |
| JP | 2009-201540 A | 9/2009 |
| WO | 2006039522 A2 | 4/2006 |

OTHER PUBLICATIONS

Japanese Office Action dated Nov. 5, 2013, with English translation.
Chinese First Office Action dated Apr. 22, 2014, with English translation.

* cited by examiner

ENDOSCOPE SYSTEM

The present application claims priority from Japanese Patent Application No. 2010-130220 filed on Jun. 7, 2010, the entire content of which is incorporated herein by reference.

BACKGROUND OF INVENTION

1. Field of the Invention

The present invention relates to an endoscope system.

2. Description of the Related Art

As a technology for signal transmission of a captured image between an endoscope and a controller connected to the endoscope, a system employing analog transmission is described in JP-A-60-55923. In this system, a noise elimination device generates positive and negative video signals on the basis of image information of a captured image and these video signals are synchronized with each other and transmitted to the controller, so that degradation in the image quality may be restored by utilizing the symmetry between these video signals. Thus, image information may be transmitted with high noise resistance and without causing a large failure in the image. In the analog transmission, however, image data to be transmitted and an ultimate image obtained at the destination are weighted in a ratio of 1:1 in general, and therefore, the degree of influence is low when disturbance of noise is weak but the degree of influence on a transmitted image is increased as the disturbance of noise is stronger. Therefore, it is necessary to sufficiently improve the noise resistance for improving the transmission performance.

In the transmission of image information, it has been also proposed to digitalize the image information and serially transmit the digitalized information in order to reduce the image quality degradation caused during the transmission (see JP-A-2009-201540 and JP-A-2008-80007). In the serial transmission of a digital signal, however, data differently weighted are transmitted in a time series, and therefore, if a highly weighted bit (namely, an upper bit) is influenced by noise, the influence appears remarkably in a received image. Furthermore, although noise may be eliminated through error correction by adding an error check code to every prescribed data in the serial data transmission, there is a limit to bits that can be corrected for errors, and if a burst error occurs, it cannot be corrected, and hence the image is unavoidably degraded.

Therefore, even when a captured image signal is serially transmitted to the controller from the endoscope for reducing the degradation in the image quality, when noise externally influences during the transmission, the influence of the noise conspicuously appears in a displayed image.

SUMMARY OF INVENTION

An object of the invention is providing an endoscope system capable of outputting high quality image information by making influence of noise inconspicuous even if a captured image signal is externally influenced by noise during serial transmission of the captured image signal from an endoscope to a controller.

According to an aspect of the invention, an endoscope system includes:

an endoscope including an imaging part that outputs a captured image signal of a subject; and a controller separated from the endoscope and connected to the endoscope through a signal line, the captured image signal output from the imaging part being serially transmitted as digital image data between the endoscope and the controller, wherein the imaging part includes a plurality of light receiving portions two-dimensionally arranged and a driving part that reads a charge signal stored in each of the light receiving portions, the driving part conducts read scan in which read of the charge signals from the light receiving portions arranged along each line extending in a main scanning direction corresponding to an arranging direction of the light receiving portions is repeated plurality of times along a sub scanning direction perpendicular to the main scanning direction, and the driving part changes an order of outputting the lines in the image data by conducting the read scan on all lines included in the captured image so as to scan some lines successively with a prescribed number of lines interlaced along the sub scanning direction and scan the other lines successively from an interlaced line with the prescribed number of lines interlaced.

DESCRIPTION OF EXEMPLARY EMBODIMENTS

Now, a preferred embodiment of the invention will be described in detail with reference to the accompanying drawings.

Figure 1:
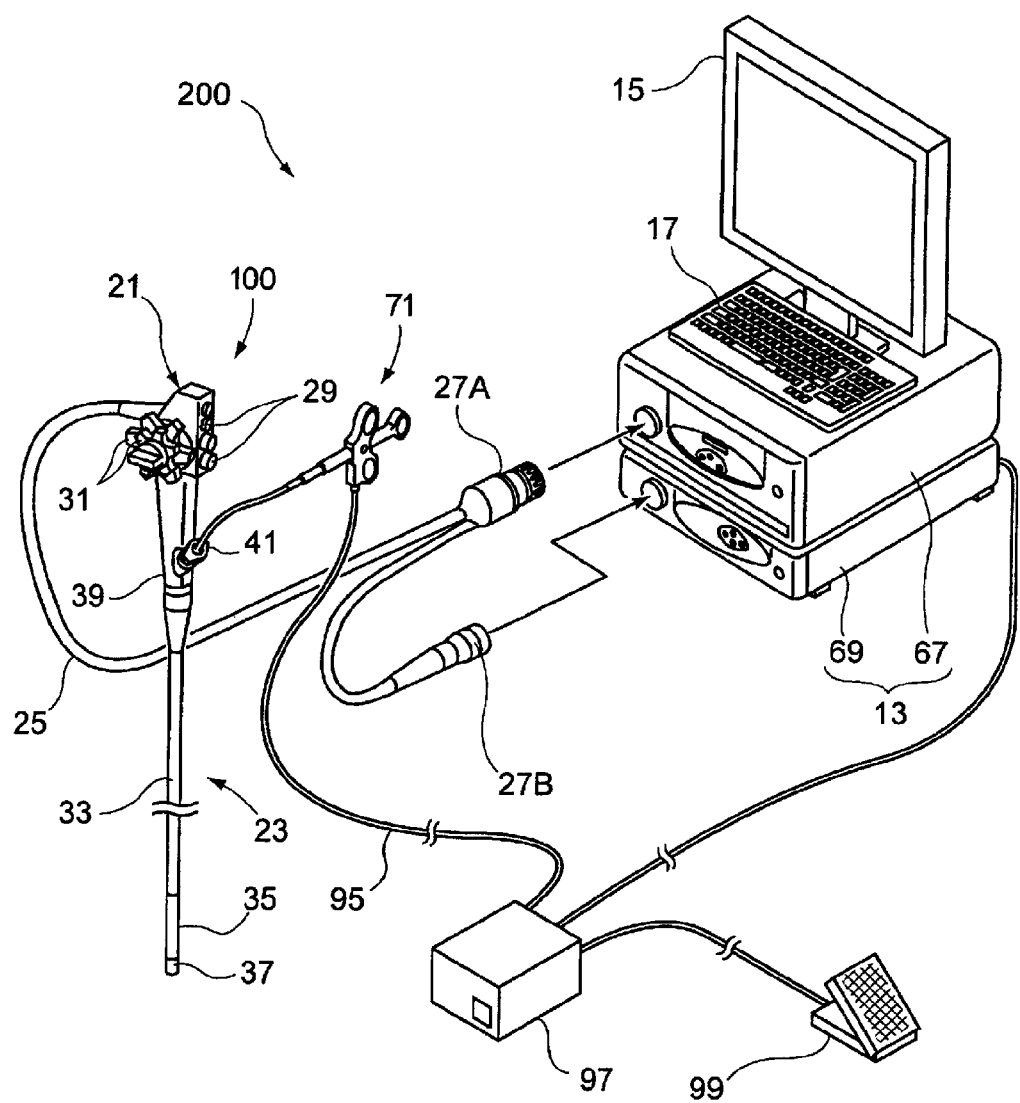
FIG. 1 is a diagram illustrating the whole structure of an endoscope system including an endoscopic device for explaining an embodiment of the invention.

FIG. 1 is a schematic diagram illustrating the whole structure of an endoscope system including an endoscopic device for explaining the embodiment of the invention.

The endoscope system 200 includes the endoscopic device (hereinafter sometimes referred to as the endoscope) 100, a controller 13 connected to the endoscope 100, a display section 15 such as a monitor, an input section 17 such as a keyboard, a treatment instrument 71, a high frequency power control section 97 for driving the treatment instrument 71, and a foot switch 99 connected to the high frequency power control section 97. The controller 13 includes a light source section 67 for supplying the endoscope 100 with illumination light and a processor section 69 for subjecting an imaging signal supplied from the endoscope 100 to various image processing for converting it into a video signal.

The endoscope 100 includes a body operating section 21, an endoscope inserting section 23 connected to the body operating section 21 to be inserted into a body cavity, a universal cord 25 connected to the body operating section 21 and containing various duct lines and signal cables, and connectors 27A and 27B provided at the tip of the universal cord 25 to be removably connected to the controller 13. The connectors 27A and 27B are individual connectors to be respectively connected to the light source section 67 and the processor section 69 of the controller 13 or may be one connector of a composite type.

The light source section 67 of the controller 13 outputs emitted light to the endoscope 100 through the connector 27A and the universal cord 25, so that illumination light may be supplied to an illuminating optical system provided at the tip of the endoscope inserting section 23.

In the body operating section 21 of the endoscope 100, various buttons 29 such as an air/water supply button, a suction button, a shutter button and a function switching button are arranged, and a pair of angle nobs 31 for bending a tip side of the endoscope are provided.

The endoscope inserting section 23 includes a soft part 33, a bending part 35 and a tip part (an endoscope tip part) 37 successively disposed in this order from the side of the body operating section 21. The soft part 33 is flexible and is connected to the base side of the bending part 35, and the bending part 35 is capable of bending when a wire (not shown) inserted through the endoscope inserting section 23 is pulled by rotating the angle nobs 31 of the body operating section 21. As a result, the endoscope tip part 37 may be made to face toward a desired direction.

Figure 2:
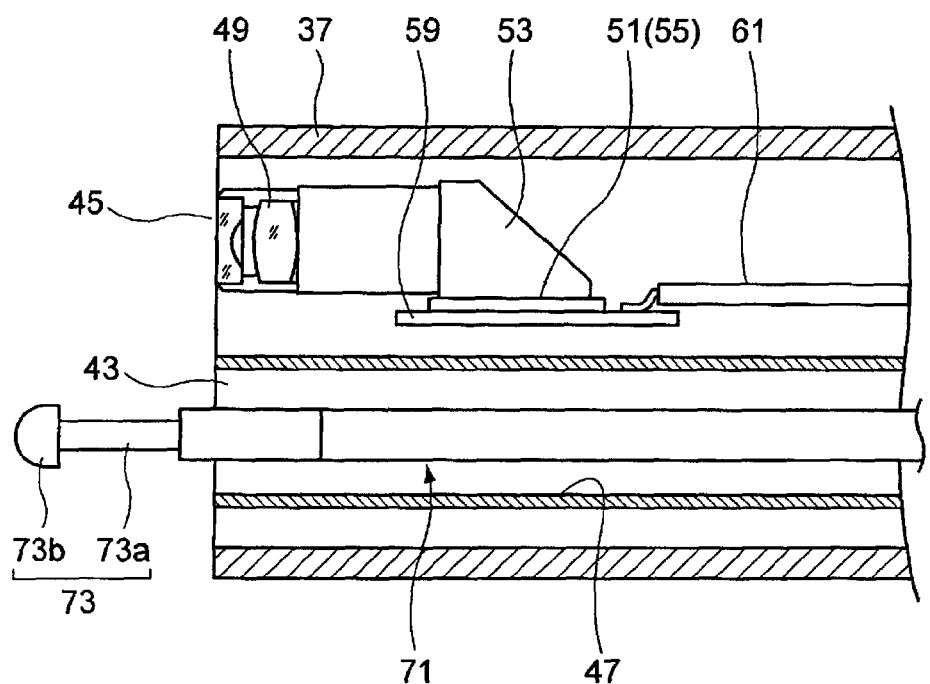
FIG. 2 is an enlarged principal part cross-sectional view illustrating a tip part of the endoscopic device.

FIG. 2 is an enlarged partial cross-sectional view illustrating the structure of the tip part of the endoscopic device. An imaging optical system provided at the tip of the endoscope inserting section 23 includes an imaging chip 51 having an imaging device 55 for capturing an image of an observed site illuminated by the illuminating optical system, and outputs an imaging signal of the observed image obtained from the imaging device 55 to the controller 13. As the imaging device 55, a CMOS (Complementary Metal Oxide Semiconductor) image sensor is used. The processor section 69 of the controller 13 displays, in the display section 15 illustrated in FIG. 1, image information obtained through image processing of the input imaging signal. The input section 17 such as a keyboard connected to the controller 13 may be used for inputting commands for such a series of processing.

The endoscope tip part 37 is provided with a lighting window (not shown) and an observation window 45 (see FIG. 2) as well as a clamp opening 43 of an instrument inserting hole 47. In the observation window 45, an objective optical system 49 including a plurality of lenses is provided for capturing an image of an observed site inside a body cavity. Behind the objective optical system 49 along the optical path, a prism 53 is connected for bending the optical axis of the objective optical system 49 at right angles to guide it toward the imaging chip 51.

The imaging chip 51 is a monolithic semiconductor (i.e., what is called a CMOS sensor chip) integrally including the imaging device 55 and a peripheral circuit 57 for driving the imaging device 55 and for inputting/outputting signals to/from the imaging device 55, and is mounted on a substrate 59. A signal line 61 is connected to the rear end of the substrate 59, and the signal line 61 is connected to the processor section 69 through the universal cord 25 illustrated in FIG. 1 so as to transfer various signals. In other words, the objective optical system 49 and the prism 53 together form an optical image obtained on the side of the endoscope tip part 37 on the imaging device 55 of the imaging chip 51, and the imaging device 55 outputs an output signal of the optical image as a captured image signal. The captured image signal is transmitted from the side of the endoscope 100 to the controller 13 through the universal cord 25.

The processor section 69 of the controller 13 subjects the captured image signal transmitted from the endoscope 100 to the image processing on the basis of a command issued from the body operating section 21 or the input part 17 of the endoscope 100, so as to generate an image for display to be supplied to the display part 15.

A connecting part 39 disposed between the body operating section 21 and the endoscope inserting section 23 is provided with a clamp inserting section 41 through which a treatment instrument such as a clamp is inserted. The aforementioned treatment instrument 71 is inserted through this clamp inserting section 41 to be guided out from the tip of the endoscope tip part 37. The treatment instrument 71 is introduced to the endoscope tip part 37 through the instrument inserting hole 47 formed through the endoscope inserting section 23 as illustrated in FIG. 2. The treatment instrument 71 is a high frequency treatment instrument that may superimpose noise on a signal line adjacently provided in this embodiment, and is connected to the high frequency power control section 97 through an electric cord 95. The high frequency power control section 97 is connected to the controller 13 and the foot switch 99 for controlling the drive of the high frequency treatment instrument 71.

The structure of the high frequency treatment instrument 71 will now be described.

Figure 3:
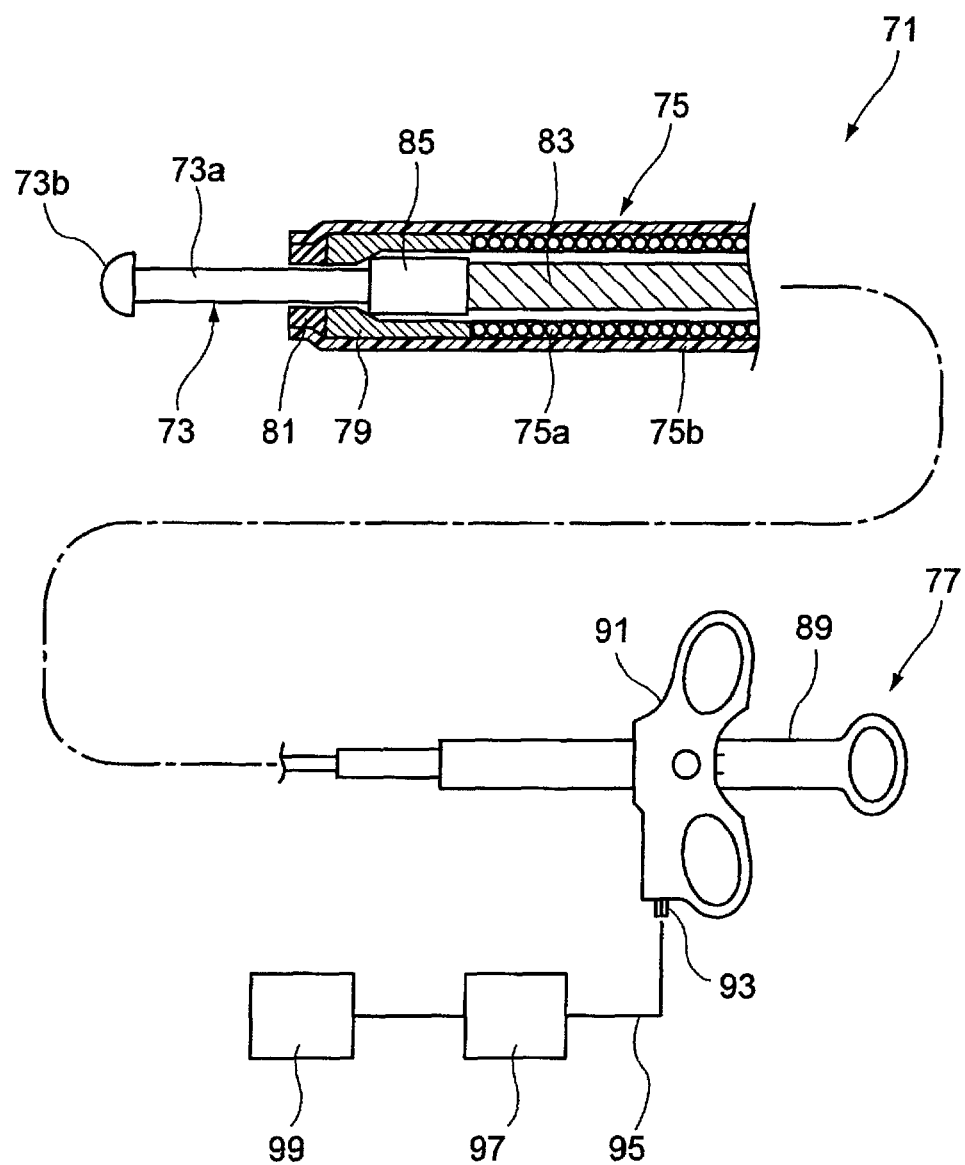
FIG. 3 is a vertical principal part cross-sectional view roughly illustrating the structure of a high frequency treatment instrument.

FIG. 3 is a vertical principal part cross-sectional view illustrating the schematic structure of the high frequency treatment instrument. As illustrated in FIG. 3, the high frequency treatment instrument 71, that is, a diathermy knife, has flexibility sufficient to be inserted into the treatment instrument inserting hole 47 of the endoscope 100 (see FIG. 2) and includes a sheath 75 containing a close wound coil 75a and an insulating tube 75b of tetrafluoroethylene or the like covering the close wound coil 75a, and an operation part 77 provided at the base end of the sheath 75. At the tip of the close wound coil 75a, a cylindrical stopper member 79 and a ring-shaped sheath tip insulating chip 81 are provided to be covered with the insulating tube 75b.

An operation wire 83 with a conducting property is provided inside the sheath 75 to be movable along the shaft direction, and a stopper receiving part 85 with a conducting property in contact with the stopper member 79 is attached to the tip of the operation wire 83. The stopper receiving part 85 is provided with and electrically connected to a high frequency electrode part 73, that is, a knife part, including a bar electrode 73a and a plate electrode 73b.

The operation part 77 of the high frequency treatment instrument 71 includes an operation shaft part 89 and a slider 91 slidable on the operation shaft part 89. The slider 91 is provided with a connector part 93 and is connected to the high frequency power control section 97 through the electric cord 95. The high frequency power control section 97 is connected to the switch 99 such as a foot switch.

The base of the operation wire 83 is extended backward through an insertion hole not shown formed in the operation shaft part 89 so as to be connected to the slider 91. When the slider 91 is slid in the shaft direction, the operation wire 83 moves backward/forward along the shaft direction inside the sheath 75, so that the bar electrode 73a of the high frequency electrode part 73 may appear/disappear from the tip of the sheath 75.

Next, signal processing performed by the endoscope system having the aforementioned structure will be described.

Figure 4:
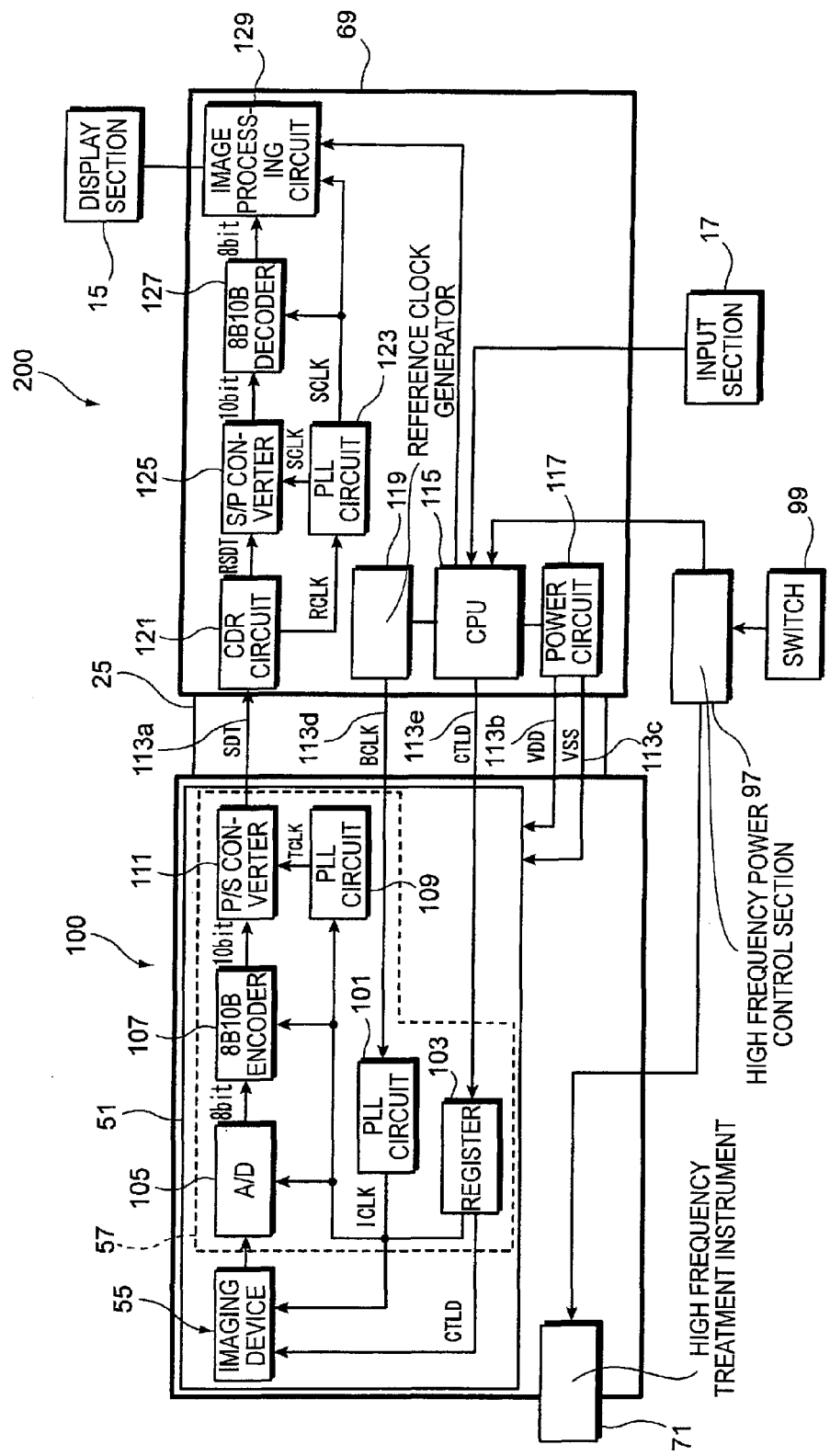
FIG. 4 is a conceptual block diagram of the endoscope system of FIG. 1.

FIG. 4 is a conceptual block diagram illustrating the configuration of the endoscope system. As illustrated in FIG. 4, the endoscope system 200 includes the endoscope 100 and the processor section 69 connected to each other through the universal cord 25. The imaging chip 51 including the imaging device 55 and the peripheral circuit 57 is built in the endoscope 100. The peripheral circuit 57 of the imaging chip 51 includes a PLL (Phase-Locked Loop) circuit 101 for generating an internal clock signal, a register 103 for setting control data in the imaging device 55, an analog/digital (A/D) converter 105 for digitalizing an imaging signal output from the imaging device 55, an 8B10B encoder 107 for subjecting the digitalized imaging signal to 8B10B type encoding, a PLL circuit 109 for generating a clock signal for serial transmission by multiplying the frequency of the internal clock signal, and a parallel/serial (P/S) converter 111 for converting the encoded imaging signal into a serial signal and outputting the serial signal.

The PLL circuit 101 is a phase locked circuit composed of a phase comparator, a loop filter, a voltage control oscillator and a frequency divider, and generates an internal clock signal ICLK in synchronization with a stable reference clock signal BCLK input from the processor section 69 and having a frequency in a prescribed proportional relationship with the frequency of the reference clock signal BCLK (i.e., having a multiplied frequency). The internal clock signal ICLK is supplied to respective portions of the peripheral circuit 57 and the imaging device 55.

The register 103 holds control data CTLD input from the processor section 69 and used for driving the imaging device 55 and inputs it to the imaging device 55. The register 103 is a shift register for performing serial/parallel conversion, and converts the control data CTLD input in the form of a serial signal into a parallel signal to be input to the imaging device 55. As the control data CTLD, a scanning method for pixels (such as a normal scanning or interleave scanning mode described in detail later), a pixel region to be scanned, a shutter speed (i.e., exposure time) and the like are input. The imaging device 55 controls a scanning circuit described later on the basis of the control data CTLD and the internal clock signal ICLK.

The A/D converter 105 converts the imaging signal output from the imaging device 55 through quantization into an 8-bit (256-scale) digital signal and inputs the converted 8-bit digital signal to the 8B10B encoder 107 in parallel by using 8 lines.

The 8B10B encoder 107 is an 8B10B type encoder for converting the 8-bit digital signal input from the A/D converter 105 into a 10-bit digital signal by adding redundant 2-bit data, and the conversion from 8-bit to 10-bit is conducted by using a translation table according to a standard.

The PLL circuit 109 has a similar configuration to the PLL circuit 101, and generates the clock signal TCLK for serial transmission by multiplying the frequency of the internal clock signal ICLK by, for example, 10 and supplies the clock signal TCLK to the P/S converter 111.

The P/S converter 111 converts the digital signal (i.e., the 10-bit parallel data) input from the 8B10B encoder 107 into 10-bit serial data in accordance with the clock signal TCLK for serial transmission generated by the PLL circuit 109. At this point, owing to the function of the PLL circuit 109, the frequency of the serial data resulting from the conversion is 10 times as high as the frequency of the parallel data obtained before the conversion. The serial data generated by the P/S converter 111 is transmitted to the processor section 69 as an imaging signal SDT through a signal line 113a running inside the universal cord 25.

The processor section 69 includes a main control circuit (CPU) 115 for controlling the whole device, a power circuit 117 for generating a power voltage VDD and a ground voltage VSS, a reference clock generator 119 for generating the reference clock signal BCLK, a clock and data recovery (CDR) circuit 121 for receiving the imaging signal SDT from the imaging chip 51 and recovering a clock signal and a data signal from the imaging signal SDT, a PLL circuit 123 for generating a clock signal for signal processing with the same frequency as the internal clock signal ICLK used in the imaging chip 51 by multiplying the frequency of the clock signal generated by the CDR circuit 121, a serial/parallel (S/P) converter 125 for converting the data signal generated by the CDR circuit 121 into a parallel signal, an 8B10B decoder 127 for generating the imaging signal obtained before the encoding by subjecting the parallelized imaging signal to 8B10B type decoding, and an image processing circuit 129 for generating image data to be displayed in the display section 15 by subjecting the decoded imaging signal to the image processing.

The power circuit 117 supplies the power voltage VDD and the ground voltage VSS to the respective portions within the processor section 69 and supplies these voltages to the respective portions within the imaging chip 51 through the signal lines 113b and 113c. The reference clock generator 119 generates the reference clock signal BCLK with a stable frequency and inputs the reference clock signal BCLK to the PLL circuit 101 included in the imaging chip 51 through a signal line 113d.

The CPU 115 controls the respective portions within the processor section 69, generates the aforementioned control data CTLD and inputs the control data CTLD to the register 103 included in the imaging chip 51 through a signal line 113e.

The CDR circuit 121 detects the phase of the imaging signal SDT serially transmitted from the imaging chip 51, generates an extraction clock signal RCLK in synchronization with the frequency of the imaging signal SDT, and generates data obtained by retiming the imaging signal SDT with the extraction clock signal RCLK (i.e., retiming data or an imaging signal RSDT) by sampling the imaging signal SDT with the extraction clock signal RCLK.

The extraction clock signal RCLK generated by the CDR circuit 121 is input to the PLL circuit 123, and the imaging signal RSDT generated by the CDR circuit 121 is input to the S/P converter 125.

The PLL circuit 123 has a similar configuration to the aforementioned PLL circuit 101, and generates the clock signal SCLK for signal processing with the same frequency as the internal clock signal ICLK by multiplying the frequency of the extraction clock signal RCLK by 1/10. The PLL circuit 123 supplies the thus generated clock signal SCLK to the S/P converter 125, the 8B10B decoder 127 and the image processing circuit 129.

The S/P converter 125 subjects the imaging signal RSDT input from the CDR circuit 121 to serial/parallel conversion, corresponding to the inverse of the parallel/serial conversion, in accordance with the clock signal SCLK generated by the PLL circuit 123, so as to generate an imaging signal of 10-bit parallel data, and inputs the imaging signal to the 8B10B decoder 127.

The 8B10B decoder 127 conducts conversion inverse to that performed by the aforementioned 8B10B encoder 107 by using a translation table according to the 8B10B standard, and decodes the imaging signal input thereto from the 10-bit signal to the 8-bit signal. The 8-bit imaging signal decoded by the 8B10B decoder 127 is input to the image processing circuit 129.

The image processing circuit 129 records the imaging signal in an internal memory on the basis of the clock signal SCLK and generates image data to be output through various image processing including white balance adjustment, gain correction, color interpolation, edge enhancement, gamma correction, color matrix calculation and the like. Furthermore, the image processing circuit 129 converts the image data into the form of a signal for displaying it in the display section 15 and outputs the signal for image display to the display section 15.

Moreover, as described above, the high frequency power control section 97 is connected to the high frequency treatment instrument 71, the CPU 115 and the switch 99, and when a foot operation of the switch 99 is conducted, a high frequency current is supplied to the high frequency treatment instrument 71 on the basis of a command issued by the CPU 115. In other words, as illustrated in FIG. 3, the high frequency current is supplied to the high frequency electrode part 73 through the operation wire 83 disposed inside the sheath 75 of the high frequency treatment instrument 71. In supplying the high frequency current, the sheath 75 is in a state inserted through the instrument inserting hole 47 of the endoscope 100, and therefore, noise tends to be superimposed onto the signal line 113a adjacently disposed within the endoscope inserting section 23 (see FIG. 1) along the instrument inserting hole 47. In the configuration of this embodiment, even if the noise influences serial data to be transmitted, the degradation in image quality of a displayed image caused by the noise may be made inconspicuous by a method described later.

Next, signal processing for generating an imaging signal by taking out a charge signal from each pixel of the imaging device 55 will be described.

Figure 5:
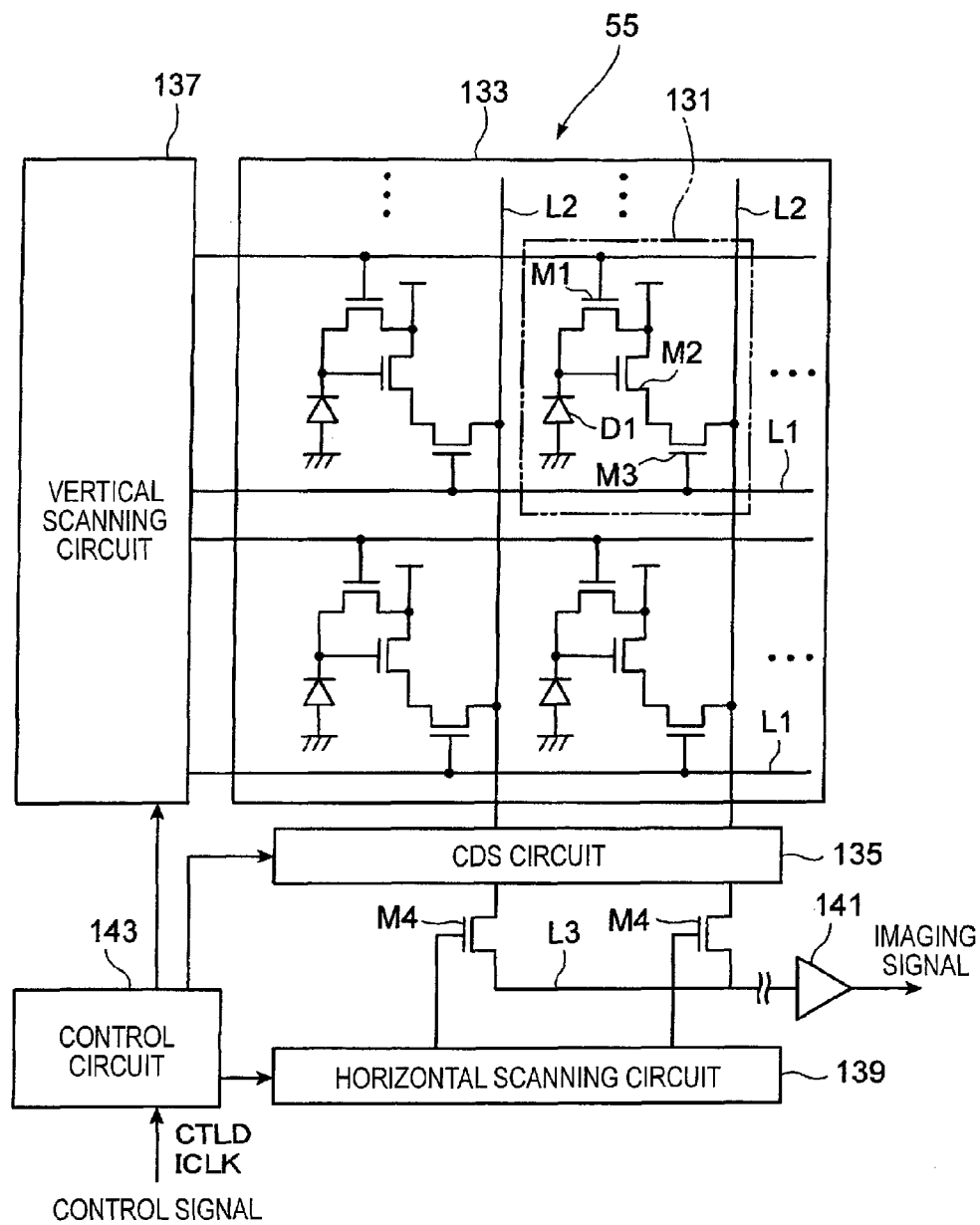
FIG. 5 is a circuit diagram illustrating the configuration of an imaging device.

FIG. 5 is a circuit diagram schematically illustrating the configuration of the imaging device 55. As illustrated in FIG. 5, the imaging device 55 includes a pixel part 133 in which unit pixels 131, that is, light receiving portions, are arranged in the form of a two-dimensional matrix, a correlated double sampling (CDS) circuit 135 for performing noise suppressing processing or the like on a charge signal corresponding to an output signal from the pixel part 133, a vertical scanning circuit 137 for controlling scan of the pixel part 133 in the vertical direction and controlling a reset operation of the pixel part 133, a horizontal scanning circuit 139 for controlling scan along the horizontal direction, an output circuit 141 for outputting a charge signal having been read, and a control circuit 143 for supplying a control signal to each of the circuits 135 through 139 and controlling timing and the like of the vertical/horizontal scan and sampling.

Each unit pixel 131 includes one photodiode D1, a transistor M1 for reset, a transistor M2 for drive (amplification) and a transistor M3 for pixel selection. Each unit pixel 131 is connected to a vertical scanning line (row selecting line) L1 and a horizontal scanning line (column selecting line) L2, and the unit pixels 131 are successively scanned by the vertical scanning circuit 137 and the horizontal scanning circuit 139.

The control circuit 143 generates a control signal to be input to the vertical scanning circuit 137 and the horizontal scanning circuit 139 for scanning the rows and the columns of the pixel part 133, a control signal to be input to the vertical scanning circuit 137 for resetting charge stored in each photodiode D1, and a control signal to be input to the CDS circuit 135 for controlling connection between the pixel part 133 and the CDS circuit 135.

The CDS circuit 135 is provided correspondingly to each column selecting line L2, so as to successively output, in accordance with a horizontal scanning signal output by the horizontal scanning circuit 139, charge signals of the respective unit pixels 131 connected to a column selecting line L1 selected by the vertical scanning circuit 137. The horizontal scanning circuit 139 controls, in accordance with the horizontal scanning signal, an on/off state of a transistor M4 for column selection provided between the CDS circuit 135 and an output bus line L3 connected to the output circuit 141. The output circuit 141 amplifies the charge signals successively sent from the CDS circuit 135 to the output bus line L3 and outputs the amplified signals. In the description given below, a signal output from the output circuit 141 is designated as an imaging signal for distinguishing it from a charge signal read from each unit pixel 131.

Although not shown in the drawings, the imaging device 55 is a single chip color sensor type imaging device including a color filter (such as a Bayer primary color filter) including a plurality of color segments.

The pixel part 133 has a square array structure in which the unit pixels 131 are arranged in the form of a matrix along the row direction and the column direction on a semiconductor substrate, wherein the column direction is the vertical direction and the row direction is the horizontal direction. Alternatively, it may have what is called honeycomb pixel arrangement in which unit pixels 131 disposed on odd-numbered rows and unit pixels 131 disposed on even-numbered rows are shifted from each other by a half pitch.

When the inside of a body cavity is observed with the endoscope system 200 having the aforementioned structure, as illustrated in FIG. 4, an imaging signal generated by the imaging device 55 is converted into an 8-bit parallel signal by the A/D converter 105 and then converted into a 10-bit parallel signal by the 8B10B encoder 107. The imaging signal of the 10-bit parallel signal is converted into a serial signal by the P/S converter 111 and then transmitted to the processor section 69 through the signal line 113a.

The processor section 69 receives the serially transmitted imaging signal at the CDR circuit 121, so that the CDR circuit 121 may generate a clock signal (i.e., an extraction clock signal RCLK) and a data signal phase locked with the clock signal (i.e., retiming data RSDT). The imaging signal RSDT generated as the retiming data by the CDR circuit 121 is converted on the basis of the extraction clock signal RCLK by the S/P converter 125 and the 8B10B decoder 127 so as to be recovered to the original 8-bit parallel signal. The imaging signal of this 8-bit parallel signal is converted into image data by the image processing circuit 129, so that a captured image may be displayed in the display section 15.

Figure 6:
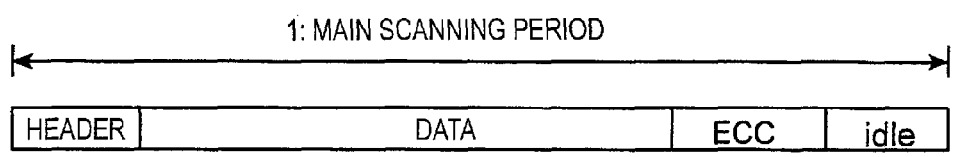
FIG. 6 is a schematic diagram illustrating a format of transmit data to be serially transmitted.

FIG. 6 illustrates an example of the format of transmit data serially transmitted. A charge signal output from the output circuit 141 is converted into serial data of this format by the peripheral circuit 57 of the imaging device 55 so as to be transmitted to the processor section 69. The serial data has a header region in front of payload including image information and an ECC (Error Check and Correct) region corresponding to detection data and an idle region behind the payload. FIG. 6 illustrates the content corresponding to one line of a captured image, and a plurality of data each corresponding to one line are serially transmitted. The information of the ECC region is provided for detecting a transmission error. Furthermore, since the detection data is attached to every line, a transmission error may be detected with respect to every line, and hence, a line having an error may be easily recovered.

Next, a method for taking out a charge signal in the imaging device 55 having the aforementioned configuration will be described in detail with reference to FIGS. 7 through 10.

The imaging device 55 may be set selectively to a normal scanning mode and an interleave scanning mode in accordance with a command issued by the CPU 115 (see FIG. 4) of the processor section 69. In the normal scanning mode, scan/read of charge signals from the respective lines of the unit pixels (photodiodes) 131 arranged in the main scanning direction is successively performed along the sub scanning direction, so as to read charge signals from the respective lines. In the interleave scanning mode, scan/read of the lines of the unit pixels 131 performed along the sub scanning direction with a prescribed number of lines interlaced is successively repeated, so as to horizontally scan all the lines for reading the charge signals.

<Normal Scanning Mode>

Figure 7:
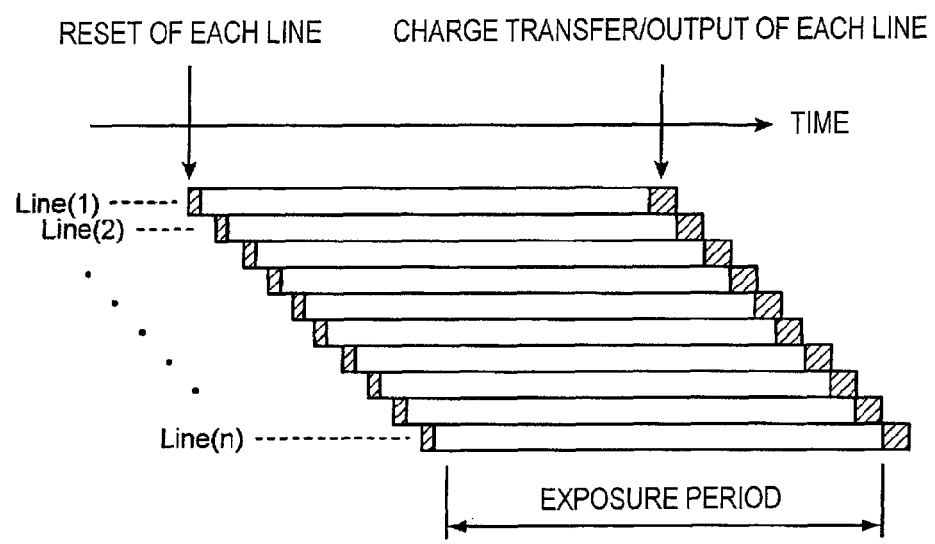
FIG. 7 is a timing chart illustrating exposing/reading timing of the imaging device in a normal scanning mode.

As illustrated in an exposing/reading timing chart of FIG. 7 for the imaging device in the normal scanning mode, in a CMOS sensor including pixel rows corresponding to scanning lines Line(1) through Line(n) (wherein n is an integer not less than 2), exposure of photodiodes is started after resetting respective unit pixels (0 through m) of each line, and after a prescribed exposure time, charge stored in the respective photodiodes is transferred for outputting charge signals. This operation is conducted successively from the scanning line Line(1) to the scanning line Line(n) in a delayed manner. In other words, in this mode, the scan/read of the respective lines of unit pixels arranged along the main scanning direction is successively conducted along the sub scanning direction for reading the charge signals, so as to generate a captured image of n rows and m columns.

Figure 8:
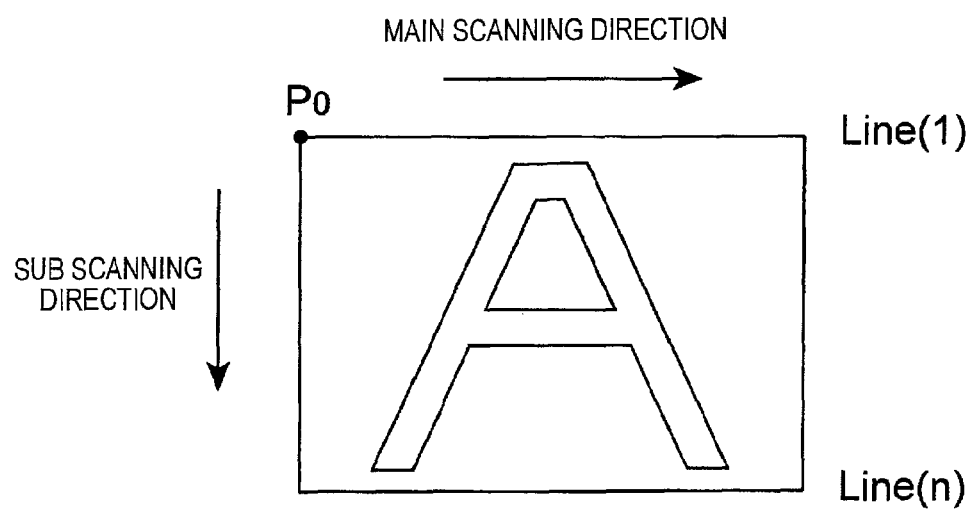
FIG. 8 is a diagram illustrating an example of a captured image.

Assuming that the content of a captured image is a letter "A", when signals output onto the output bus line L3 by repeating the scan of unit pixels along the main scanning direction from an image origin P0 and the scan along the sub scanning direction are changed into image data in the output order, an image as illustrated in FIG. 8 is obtained.

<Interleave Scanning Mode>

Figure 9:
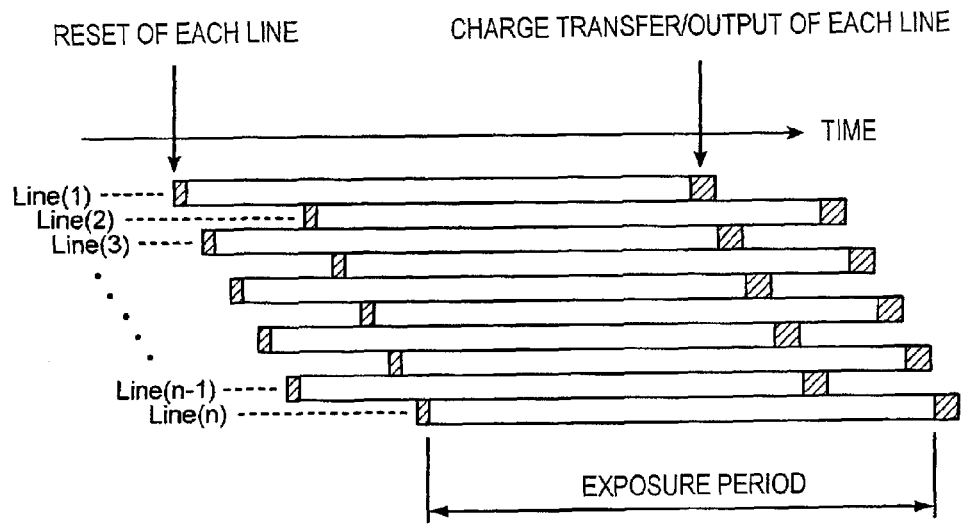
FIG. 9 is a timing chart illustrating exposing/reading timing of the imaging device in an interleave scanning mode of 1-line interlaced scan.

FIG. 9 illustrates an example of resetting, exposing and reading timings for an imaging device using a rolling shutter in a 1-line interlaced scanning mode, that is, a kind of the interleave scanning mode. As illustrated in FIG. 9, a reset signal is output to each transistor M1 for reset (see FIG. 5) of the scanning line Line(1) from the vertical scanning circuit 137, so as to reset charge stored in the respective photodiodes D1 disposed on the scanning line Line(1) and to start charge storage (exposure). Thereafter, with one line interlaced along the vertical direction (i.e., the sub scanning direction), the scanning line Line(3) is reset and started to be charged in the same manner. Furthermore, with one line interlaced along the vertical direction, the scanning line Line(5) is reset and started to be charged, and such an operation is repeatedly conducted.

When there is no line to be interlaced, the scan starts from the scanning line Line(2) again, and after resetting the scanning line Line(2) and starting the charge storage thereof, one line is interlaced along the vertical direction, and the scanning line Line(4) is reset. Such reset processing is repeated up to the scanning line Line(n) (wherein n is the total number of the scanning lines). In this manner, charge signals stored in the unit pixels 131 of the respective lines are once discharged, and thereafter, the charge storage is started.

After a prescribed charge storage time, charge signals stored in the unit pixels 131 are output to the CDS circuit 135 (see FIG. 5). Therefore, in accordance with a selection signal to each transistor M3 for pixel selection input through the row selecting line L1 and a reading signal input from each column selecting transistor M4 for column selection input through the column selecting line L2, the charge signals of the respective unit pixels 131 are output to the output bus line L3 (see FIG. 5) in the order of scanning lines Line(1), Line(3), Line(n−1), Line(2), Line(4), ..., and Line(n).

In other words, in this interleave scanning mode, first read scan in which a first line not scanned yet is selected for horizontal scan for reading charge signals from respective light receiving portions corresponding to the first line and second read scan in which a second line not scanned yet interlaced by a prescribed number of lines from the first line along the sub scanning direction is selected for the horizontal scan for reading charge signals from respective light receiving portions corresponding to the second line are repeated down to the lower end of the sub scanning direction while keeping the prescribed number of lines as the interval between the first line and the second line, and thereafter, the first read scan and the second read scan are repeated down to the lower end of the sub scanning direction again with a line not scanned yet selected from the upper end of the sub scanning direction, and such a process is repeated plural times.

Figure 10:
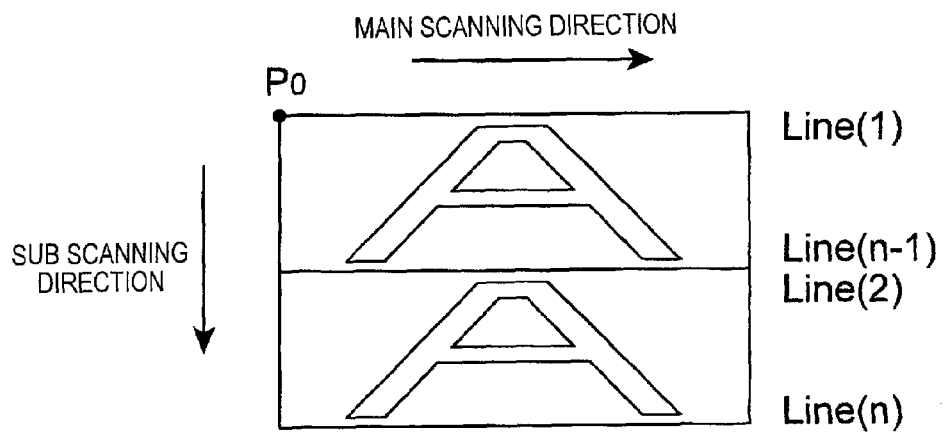
FIG. 10 is a diagram illustrating a captured image generated in accordance with the reading order of charge signals in the interleave scanning mode of FIG. 9.

Assuming that the content of a captured image is a letter "A" as illustrated in FIG. 8, in the case where the aforementioned output order of the charge signals is employed, when signals output onto the output bus line L3 by repeating the scan along the main scanning direction from an image origin P0 and the scan with one line interlaced along the sub scanning direction are changed into image data in the output order, image data halved along the sub scanning direction as illustrated in FIG. 10 is obtained.

In other words, the signals are output in a time series in the successive and continuous order of the respective lines of a captured image in the sub scanning direction in the normal scanning mode, while the signals are output in the discontinuous order of the lines in a captured image in the interleave scanning mode. Therefore, in the interleave scanning mode, even when an error is caused in part of an imaging signal during the transmission, a region having the error appears as discontinuous lines not adjacent to each other in a displayed image, and hence, degradation of the image quality caused by the error is inconspicuous.

Figure 11:
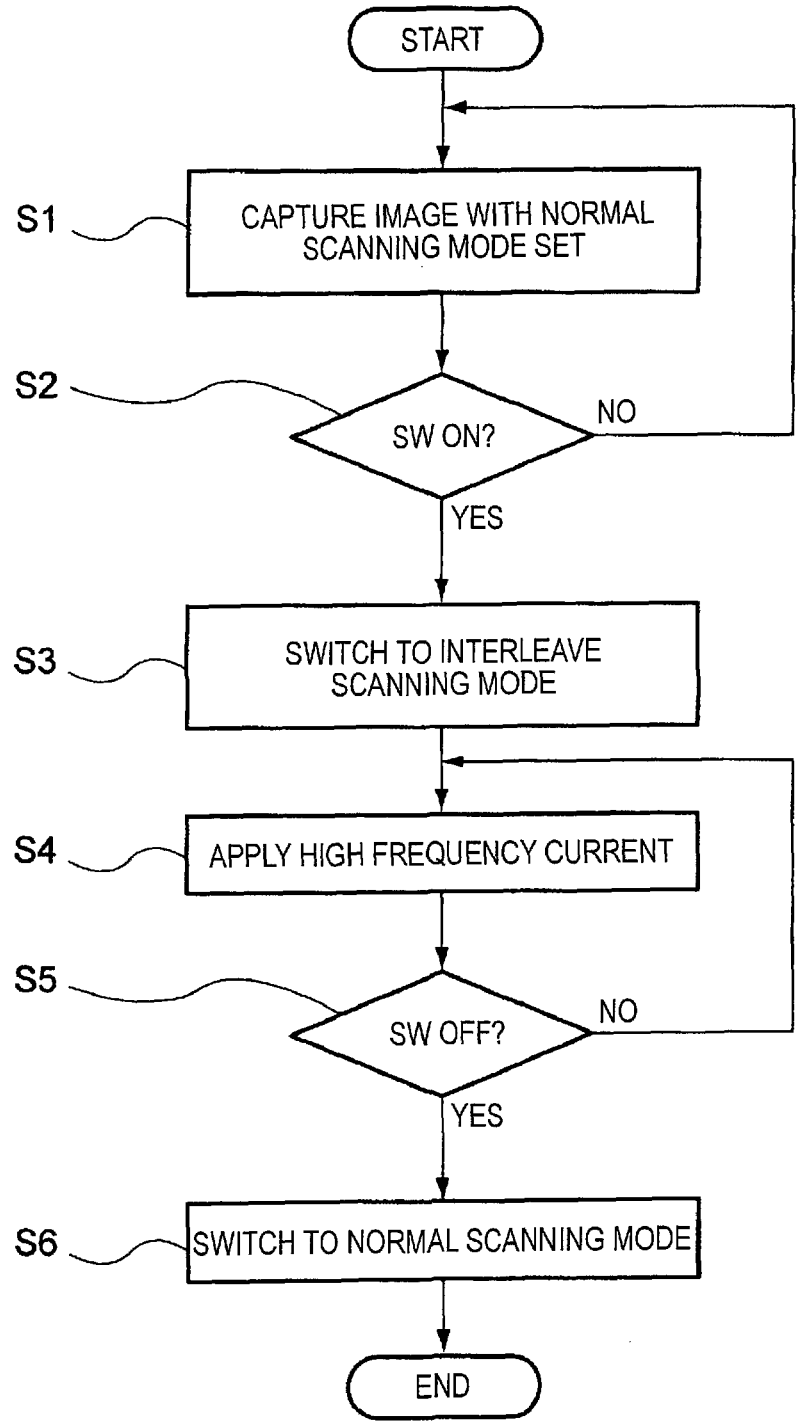
FIG. 11 is a flowchart illustrating procedures in switching between the normal scanning mode and the interleave scanning mode.

FIG. 11 is a flowchart illustrating procedures in switching between the normal scanning mode and the interleave scanning mode. In the case where influence of external noise is feared during the transmission of serial data, the normal scanning mode is switched to the interleave scanning mode. This mode switching is conducted at timing of the operation of the high frequency treatment instrument 71 for eliminating the influence of noise caused during the operation of the high frequency treatment instrument 71. Specifically, since a high frequency current is applied for operating the high frequency treatment instrument 71 while the switch 99 is in an on state, the interleave scanning mode is set during the on operation.

In FIG. 11, the normal scanning mode is set for capturing an image in step S1, it is determined in step S2 whether or not the switch 99 is in an on state (namely, whether or not the switch has been operated), and when it is in an off state, it is determined that the high frequency treatment instrument 71 is not operated and hence the normal scanning mode is retained. When it is determined that the switch 99 is in an on state, the normal scanning mode is switched to the interleave scanning mode in step S3. After switching to the interleave scanning mode, a high frequency current is applied to the high frequency treatment instrument 71 in step S4, so as to perform a treatment such as incision of a tissue. Subsequently, it is determined in step S5 whether or not the switch 99 is in an off state, and when it is in an on state, the interleave scanning mode is retained. When it is in an off state, it is determined that the treatment with the high frequency treatment instrument 71 has been completed, and hence the interleave scanning mode is switched to the normal scanning mode in step S6.

Figure 12:
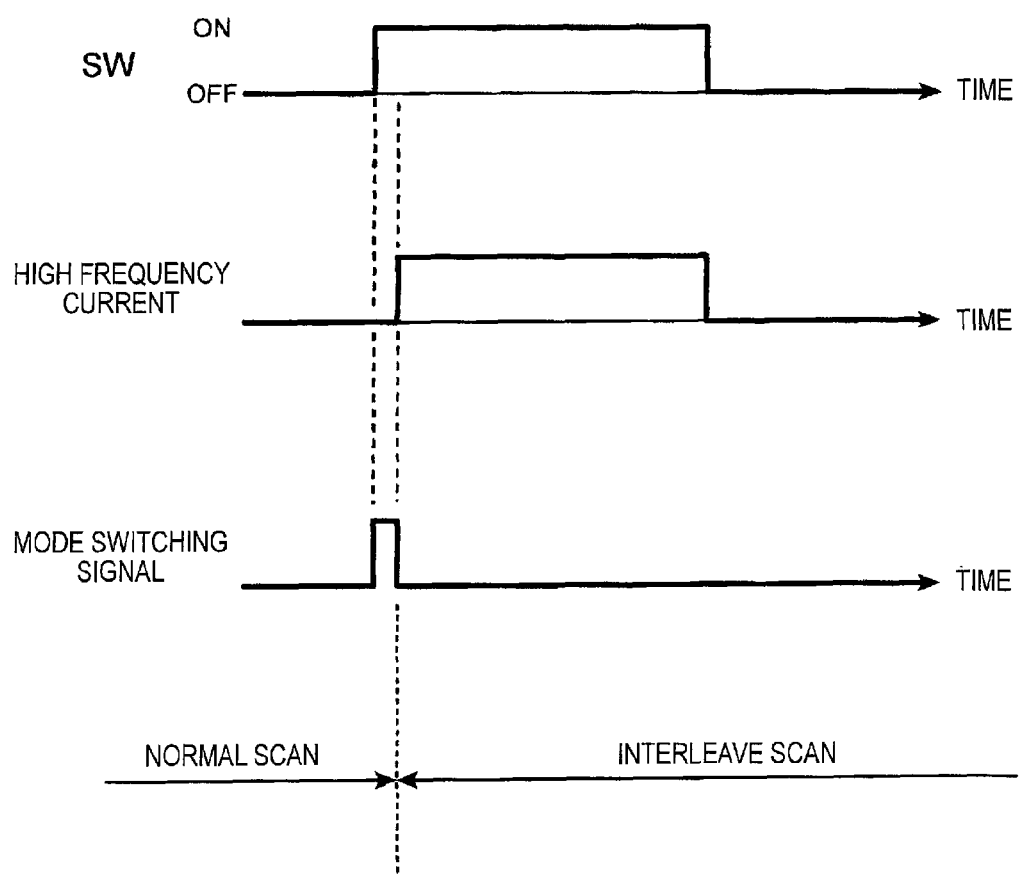
FIG. 12 is a timing chart illustrating timing of switching from the normal scanning mode to the interleave scanning mode.

FIG. 12 is a timing chart illustrating timing of switching the normal scanning mode to the interleave scanning mode under control as illustrated in FIG. 11. When the switch 99 is operated to be placed in an on state, the CPU 115 detects the on state and hence sends a mode switching signal to the register 103 (see FIG. 4), so as to switch the normal scanning mode to the interleave scanning mode. After completing the mode switching, the high frequency power control section 97 applies a high frequency current to the high frequency treatment instrument 71. In this manner, prior to the application of the high frequency current to the high frequency treatment instrument 71, the switching from the normal scanning mode to the interleave scanning mode is completed, and therefore, the influence of high frequency noise on a displayed image is definitely reduced.

Figure 13:
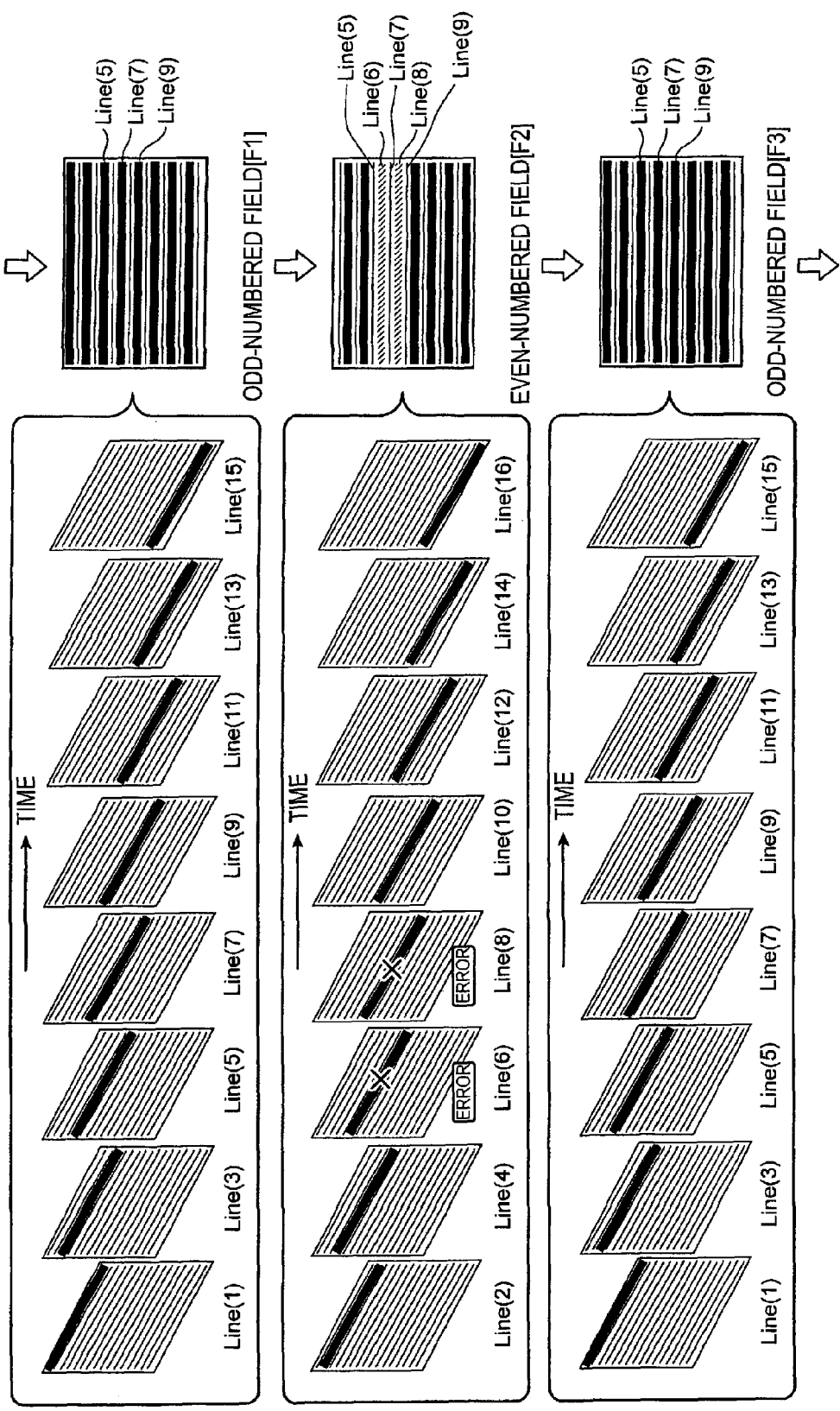
FIG. 13 is an explanation diagram of a displayed image obtained in the interleave scanning mode of FIG. 9.

FIG. 13 is an explanatory diagram of an image displayed in the interleave scanning mode. An image obtained by the imaging device 55 is displayed in the display section 15 (see FIGS. 1 and 4) with its fields switched in a short period of time in the order of an odd-numbered field F1, an even-numbered field F2, an odd-numbered field F3, etc. At this point, it is assumed for simplifying the description that one frame image includes 16 lines, that the odd-numbered field F1 includes 8 lines Line(1) through Line(15) and that the even-numbered field F2 includes 8 lines Line(2) through Line(16) as illustrated in FIG. 13.

An error caused due to influence of noise during the transmission of serial image data occurs at continuous timing from the viewpoint of the transmission order of the serial image data. In the case where transmitted signals correspond to interleave scanned data, when the data is displayed in the display section 15, the error is not displayed over adjacent lines or over a plurality of fields continuous in a time series. Specifically, as illustrated in FIG. 13, assuming that an error is caused during the transmission of the lines Line(6) and Line(8) of the even-numbered field F2, this error appears as an image having a loss of image information of the lines Line(6) and Line(8) of the even-numbered field F2.

In displaying the even-numbered field F2, however, since an after image of the previous odd-numbered field F1 visually remains, information of the lines Line(5), Line(7) and Line(9) free from the error is substantially displayed before and after the lines Line(6) and Line(8). Therefore, the lines Line(6) and Line(8) having a loss due to the error are not displayed adjacent to each other (as upper and lower lines continuous along the sub scanning direction) in the screen but are displayed in a state sandwiched between the lines free from the error. Furthermore, immediately after the display timing of the even-numbered field F2 having the error, the screen of the next odd-numbered field and successively the screen of the next even-numbered field are replaced to be displayed. Therefore, even when an error is caused, a loss minimally appears continuously over a plurality of fields continuous in a time series, and even if the loss is continuously displayed over a plurality of fields, it appears in different positions on the screen, and hence, the error is never visually recognized conspicuously. Accordingly, even if an error is caused in part of data due to the influence of noise, it may be made visually inconspicuous.

(Alternate Example of Control)

Another example of the control method for the endoscope system will now be described with reference to FIGS. 14 through 16. In the endoscope system 200 controlled by this method, the normal scanning mode is switched to the interleave scanning mode in detecting an error occurring in transmitted serial data.

Figure 14:
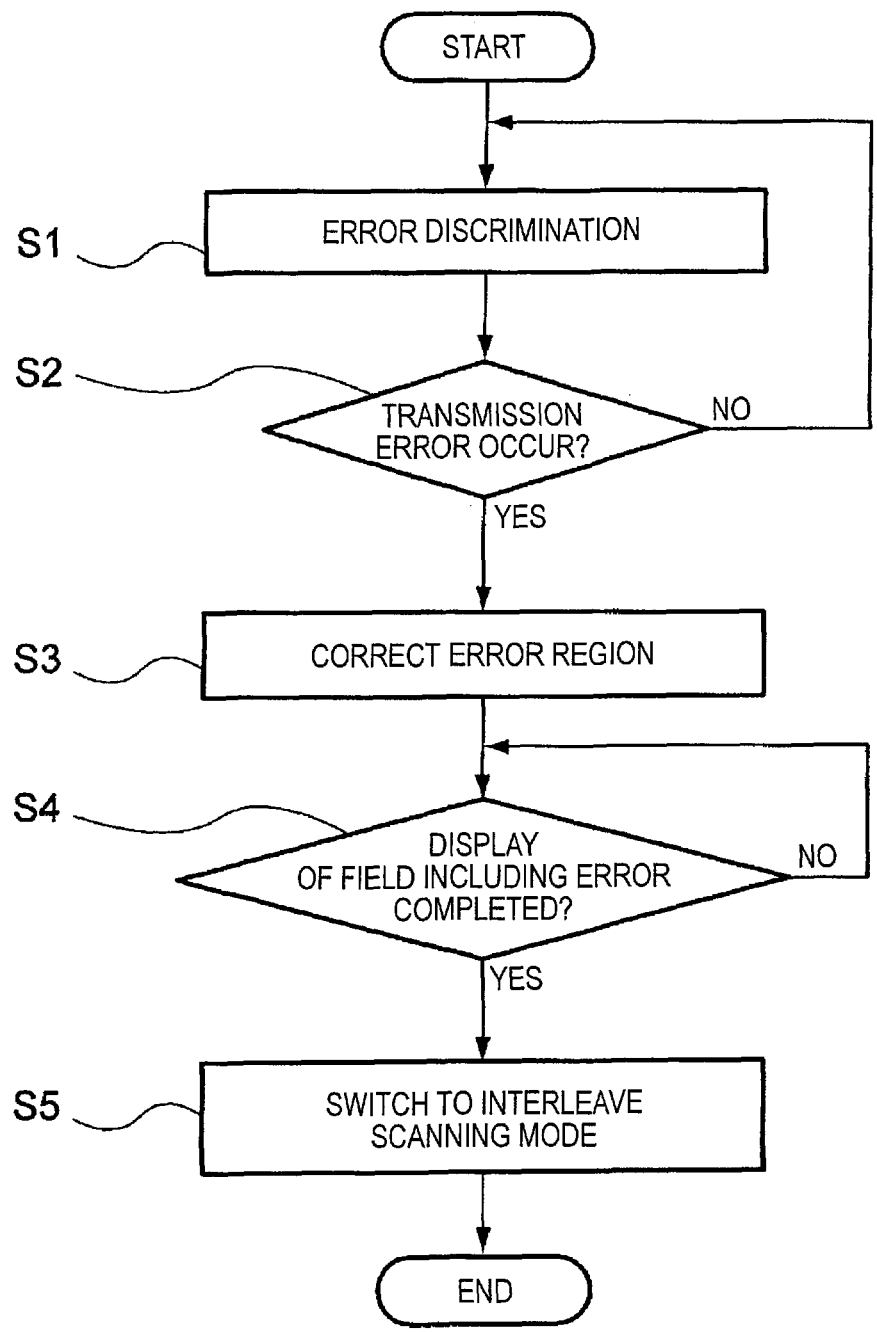
FIG. 14 is a flowchart illustrating procedures in switching to the interleave scanning mode.
Figure 15:
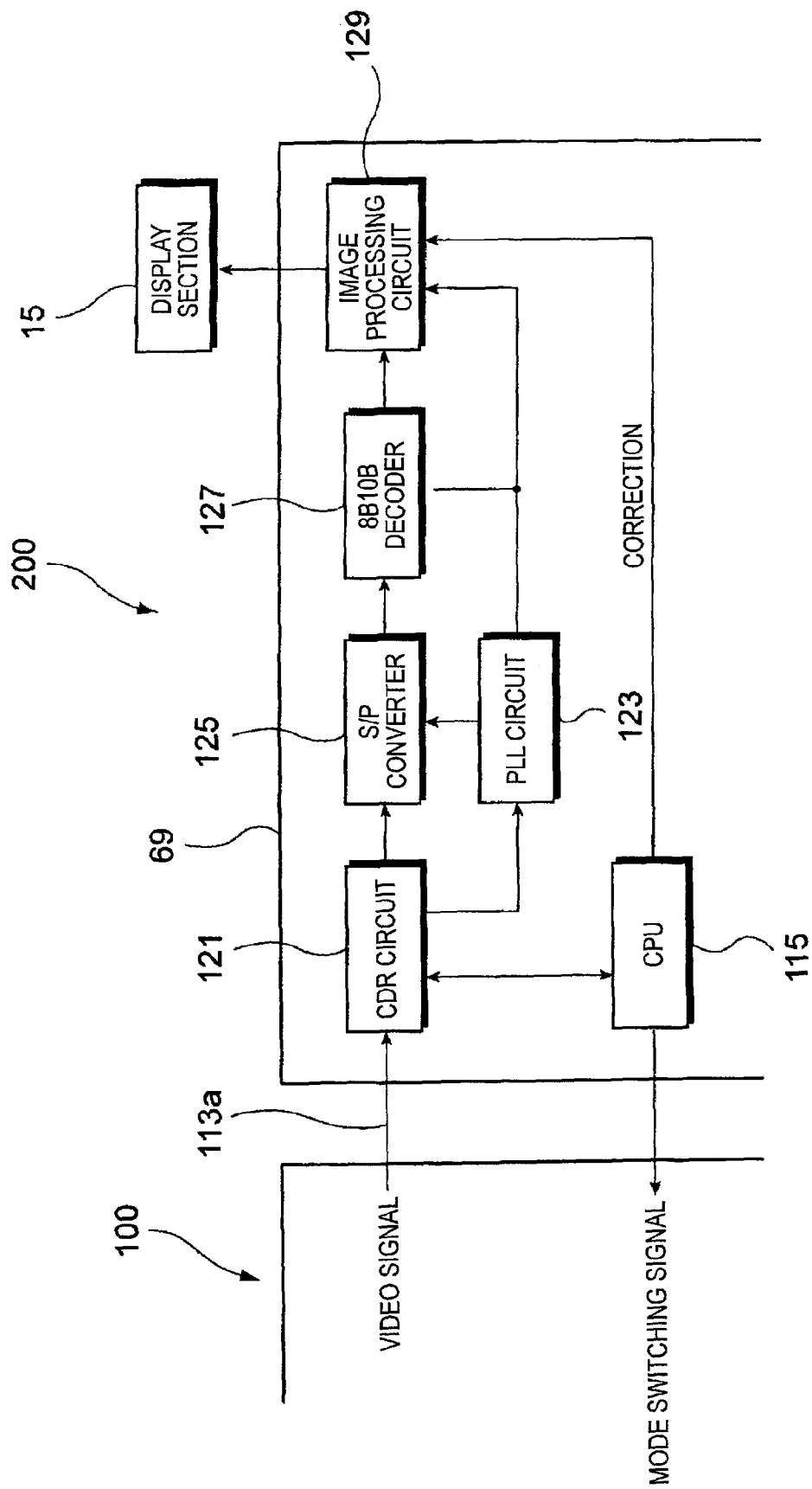
FIG. 15 is a conceptual block diagram illustrating a principal part of the endoscope system.
Figure 16:
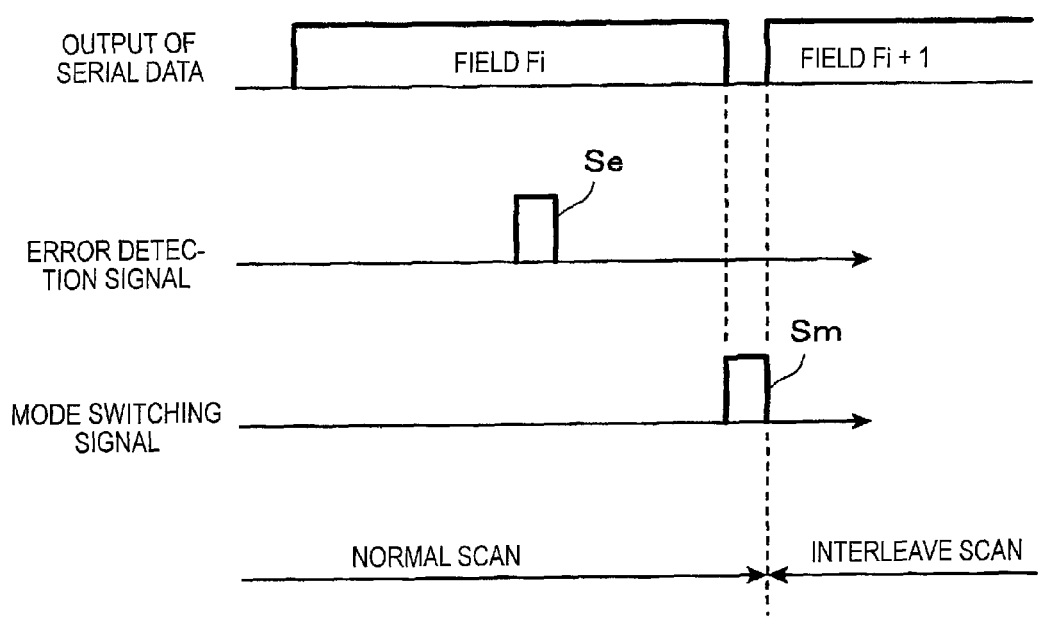
FIG. 16 is a timing chart illustrating timing of switching from the normal scanning mode to the interleave scanning mode of FIG. 14.

FIG. 14 is a flowchart illustrating procedures in the switching to the interleave scanning mode, FIG. 15 is a schematic block diagram conceptually illustrating the principal part of the endoscope system and FIG. 16 is a timing chart illustrating timing of switching the normal scanning mode to the interleave scanning mode. The procedures in this control method will now be described with reference to the flowchart of FIG. 14. In this control method, the control circuit 143 (see FIG. 5) of the imaging device 55 conducts the scan in the normal scanning mode in which the lines extending along the main scanning direction are scanned and read in the sub scanning direction, so that the imaging signal SDT may be transmitted from the endoscope 100 to the processor section 69 through the signal line 113a as illustrated in FIG. 15. The imaging signal SDT has the aforementioned data format illustrated in FIG. 6, and in this control method, occurrence of a transmission error is detected by utilizing information of the ECC (Error Check and Correct) region provided behind the payload including the image information. Specifically, on the receiving side of the data transmission, the CDR circuit 121 illustrated in FIG. 15 performs transmission error discrimination on the image information of the payload on the basis of the information of the ECC region (step S1). When an error is detected (YES in step S2), an error detection signal is sent to the CPU 115, so as to correct an error region (step S3). At this point, a field in which the error has been detected is scanned without switching the scanning mode until the scan of all the lines of this field is completed.

The image processing circuit 129 converts transmitted video signals into two-dimensional image data and makes the display section 15 to display the data. The display section 15 displays the image regardless of the occurrence of an error, and the line having an error is displayed by a same color filling method in which the whole line is filled with the same color of gray or the like.

Subsequently, when the image display of the field including the error region is completed (YES in step S4), the CPU 115 sends a mode switching signal to the register 103 of the endoscope 100, so as to switch the normal scanning mode to the interleave scanning mode (step S5). It is noted that the image information of the payload may be recovered if necessary in the correction of the error region performed in step S3.

The aforementioned procedures will be described with reference to the timing chart of FIG. 16.

The control circuit 143 of the imaging device 55 reads charge signals of the unit pixels 131 (see FIG. 5) in the normal scanning mode, and the endoscope 100 serially transmits a video signal generated on the basis of the charge signals to the processor section 69. When the CDR circuit 121 of the processor section 69 detects an error in the video signal during the transmission, namely, when an error detection signal Se is input to the CPU 115, the CPU 115 reads, still in the normal scanning mode, the charge signals of all the lines of an image of a field Fi where the error has been detected, so as to complete the serial transmission. Thereafter, when the transmission of the image of the field $F_i$ is completed, the CPU 115 outputs a mode switching signal Sm for switching the scanning mode to the endoscope 100, and the control circuit 143 of the imaging device 55 of the endoscope 100 switches the scanning mode from the normal scanning mode to the interleave scanning mode on the basis of the mode switching signal Sm. After the mode switching, the control circuit 143 reads the charge signals of a field $F_{i+1}$ in the interleave scanning mode.

In this manner, the charge signals are read with the scanning mode switched to the interleave scanning mode from the field $F_{i+1}$ next to the field where the error has been detected, and hence, the influence of noise may be made inconspicuous after the occurrence of the error.

In the format of the serial data, functions to detect, correct and compensate a transmission error are preferably provided in order to improve the noise resistance during the digital transmission. As the function to detect an error, not only the aforementioned ECC region but also cyclic redundancy check (CRC), invalid code detection (such as detection of a code undefined by the 8B10B encoding), invalid format detection or the like may be employed.

As the function to correct an error, forward error correction (FEC) such as BCH code may be employed. For an error that may not be corrected by the FEC, any of various methods may be appropriately employed including not only the aforementioned overwriting method by the same color filling method but also previous line interpolation in which an error is interpolated by using a value of the previous line of the same frame, previous frame interpolation in which an error is interpolated by using a value of a line in the same position in the previous frame, or previous/following line interpolation in which an error is interpolated by using values of previous and following lines.

The present invention is not limited to the aforementioned embodiment but it is to be understood by those skilled in the art that various changes and modifications may be made in the invention without departing from the spirit and scope thereof.

For example, although the above-described serial data is generated in the interleave scanning mode in which the order of reading the charge signals of the imaging device is changed, the order of the signals of the respective lines may be changed by another method apart from the control of the reading order of the charge signals. For example, the charge signals of the imaging device may be read in the normal scanning mode to be stored once in a memory, and the charge signals of the respective lines may be read from this memory in an order corresponding to that employed in the interleave scanning mode, so as to generate serial data.

Furthermore, although the scan read is conducted with one line interlaced in the interleave scanning mode of the aforementioned configuration example, the invention is not limited to this but two or more lines may be interlaced or lines may be randomly read.

Moreover, although the imaging device is described as a CMOS image sensor, the imaging device is not limited to this but may be a CCD (Charge Coupled Device) image sensor when a memory is used together as described above.

As described so far, the following are herein disclosed:
(1) According to an aspect of the invention, an endoscope system includes:
an endoscope including an imaging part that outputs a captured image signal of a subject; and
a controller separated from the endoscope and connected to the endoscope through a signal line, the captured image signal output from the imaging part being serially transmitted as digital image data between the endoscope and the controller,
wherein the imaging part includes a plurality of light receiving portions two-dimensionally arranged and a driving part that reads a charge signal stored in each of the light receiving portions,
the driving part conducts read scan in which read of the charge signals from the light receiving portions arranged along each line extending in a main scanning direction corresponding to an arranging direction of the light receiving portions is repeated plurality of times along a sub scanning direction perpendicular to the main scanning direction, and
the driving part changes an order of outputting the lines in the image data by conducting the read scan on all lines included in the captured image so as to scan some lines successively with a prescribed number of lines interlaced along the sub scanning direction and scan the other lines successively from an interlaced line with the prescribed number of lines interlaced.

In this endoscope system, digital image data serialized by changing the output order of the respective lines is transmitted, and hence, even when an error is caused in part of the data during the transmission due to influence of noise, the error thus caused may be made visually inconspicuous. Specifically, the driving part is set to the scanning mode in which the scan read with a prescribed number of lines interlaced along the sub scanning direction is repeated. According to the captured image signal generated in this scanning mode, a plurality of field screens formed with the prescribed number of lines interlaced are generated as sequential data. In the case where a loss is caused in the captured image signal because of an error occurring in part of the sequential data, the loss is merely a loss of part of data continuous in the sequential data and never appears over lines adjacent to each other or over a plurality of field screens continuous in a time series in the captured image. In other words, lines adjacent to each other in a captured image are not continuously present and field screens continuous in a time series are not continuously present in a specific narrow data portion continuous in sequential data, and therefore, a lack of adjacent lines and a defect caused in field screens continuous in a time series, which are visually conspicuous, may be avoided. Accordingly, when the captured image signal including the error and having been serially transmitted is displayed, the loss of the data appears, for example, in a specific field screen alone, and the field screen having the loss is immediately replaced with a next field screen. Furthermore, the loss of the data never appears as adjacent lines in the captured image but appears in positions away from each other correspondingly to the prescribed number of lines.

(2) In the endoscope system of (1), the driving part is switched between (i) a first scanning mode in which the scan read is conducted successively on every line along the sub scanning direction and (ii) a second scanning mode in which the scan read is conducted on all the lines included in the captured image by scanning some lines successively with a prescribed number of lines interlaced along the sub scanning direction and scanning the other lines successively from an interlaced line with the prescribed number of lines interlaced.

In this endoscope system, since the first scanning mode and the second scanning mode may be freely switched, each of the scanning modes may be selectively employed, so as to switch the scanning mode at necessary timing for serially transmitting generated image data.

(3) The endoscope system of (1) or (2), may further include a disturbance detecting unit that detects disturbance that is an error occurrence factor during the serial transmission; and a controlling unit that switches the driving part from the first scanning mode to the second scanning mode when the disturbance detecting unit detects occurrence of disturbance.

In this endoscope system, when disturbance occurs, the scanning mode is switched to a mode in which the image data transmission is minimally influenced by an error derived from the disturbance, and hence, the quality of a displayed image may be kept high.

(4) In the endoscope system of (3), the disturbance detecting unit detects application timing of a high frequency current to a high frequency treatment instrument that is inserted into the subject together with an inserting portion of the endoscope and has a high frequency electrode exposed at a tip thereof, and the controlling unit switches the driving part from the first scanning mode to the second scanning mode based on the application timing of the high frequency current detected by the disturbance detecting unit.

Although noise tends to be caused in a signal line in performing a treatment with a high frequency treatment instrument at timing of turning on the high frequency treatment instrument, when the first scanning mode is switched to the second scanning mode in this endoscope system, even if a loss of data is caused by the occurrence of noise, the loss may be made visually inconspicuous. As a result, regardless of the operation of the high frequency treatment instrument, a good captured image may be always provided.

(5) In the endoscope system of (3) or (4), in the digital image data serially transmitted, the captured image signal is divided correspondingly to each of the lines and detection data that detects a transmission error is provided to every divided line, and the controlling unit detects occurrence of a transmission error by using the detection data and switches the driving part from the first scanning mode to the second scanning mode on the basis of timing of detecting the transmission error.

In this endoscope system, since the detection data is provided to every line, the occurrence of a transmission error may be detected with respect to every line, and hence, a line having an error may be easily recovered. Furthermore, since the first scanning mode is switched to the second scanning mode on the basis of the timing of the detection of the occurrence of a transmission error, an error occurring at arbitrary timing may be coped with at any time for switching an appropriate mode, and therefore, a good captured image may be always provided.

(6) In the endoscope system of (1) through (5), the prescribed number of lines to be interlaced is one line interlaced.

In this endoscope system, since the scan read is conducted alternately on every line, a field of odd-numbered lines and a field of even-numbered lines are alternately obtained. Therefore, an image may be displayed according to a normal NTSC display method.

(7) The endoscope system of (1) through (5), may further include: a display part that displays image information obtained based on the captured image signal serially transmitted.

In this endoscope system, obtained information of a captured image may be displayed in the display part in a state where a loss of data is minimally conspicuous.

<Additional Remarks>

In the endoscope system, the control means switches the driving part from the first scanning mode to the second scanning mode before supplying a high frequency current to the high frequency treatment instrument.

In this endoscope system, the driving part is switched to the second scanning mode before supplying the high frequency current to the high frequency treatment instrument, and therefore, a loss of data caused by the occurrence of noise may be made inconspicuous at timing at which noise tends to be caused in a signal line. Thus, a good captured image may be always stably supplied.

In the endoscope system, the control means switches the driving part from the first scanning mode to the second scanning mode after completing read scan of whole of the captured image in which the transmission error has been detected.

In this endoscope system, since the driving part is switched to the second scanning mode after completing the read scan of the captured image in which the transmission error has been detected, a loss of data caused by the occurrence of the transmission error may be made inconspicuous in the captured image transmitted after the occurrence of the transmission error without complicating the read scan process. Thus, a good captured image may be stably supplied.

The endoscope system of the invention includes an endoscope equipped with an imaging part for outputting a captured image signal of a subject; a controller separated from the endoscope and connected to the endoscope through a signal line, for serially transmitting digital image data including the captured image signal between the endoscope and the controller; and interleave image data generating means for generating interleave image data in which all horizontal lines of a captured image obtained based on the captured image signal of the subject are rearranged by rearranging some horizontal lines of the captured image with a prescribed number of lines interlaced along a vertical direction of the captured image and rearranging the other horizontal lines with the prescribed number of lines interlaced from one interlaced horizontal line.

In this endoscope system, a loss of data caused by the occurrence of the transmission error may be made inconspicuous in the captured image not by employing a driving method in which the order of reading charge signals from the imaging part is changed but by employing a driving method performed in a normal successive order of lines.

What is claimed is:

1. An endoscope system comprising:
an endoscope including an imaging part that outputs a captured image signal of a subject; and
a controller separated from the endoscope and connected to the endoscope through a signal line, the captured image signal output from the imaging part being serially transmitted as digital image data between the endoscope and the controller,
wherein the imaging part includes a plurality of light receiving portions two-dimensionally arranged and a driving part that reads a charge signal stored in each of the light receiving portions,
wherein the driving part conducts a read scan in which a read of the charge signals from the light receiving portions arranged along each line extending in a main scanning direction corresponding to an arranging direction of the light receiving portions is repeated a plurality of times along a sub scanning direction perpendicular to the main scanning direction, wherein the driving part changes an order of outputting lines in the digital image data by conducting the read scan on all lines included in a captured image so as to scan some lines successively with a prescribed number of lines interlaced along the sub scanning direction and scan the other lines successively from an interlaced line with the prescribed number of lines interlaced, wherein, in the digital image data serially transmitted, the captured image signal is divided correspondingly to each of the lines and detection data that detects a transmission error is provided to every divided line, wherein the controlling unit detects an occurrence of a transmission error by using the detection data and switches the driving part from a first scanning mode to a second scanning mode on a basis of timing of detecting the transmission error, wherein the driving part is switched between the first scanning mode in which the read scan is conducted successively on every line along the sub scanning direction and a second scanning mode in which the read scan is conducted on all the lines included in the captured image by scanning some lines successively with a prescribed number of lines interlaced along the sub scanning direction and scanning the other lines successively from an interlaced line with the prescribed number of lines interlaced, said endoscope system further comprising:

a disturbance detecting unit that detects a disturbance that is an error occurrence factor during a serial transmission; and a controlling unit that switches the driving part from the first scanning mode to the second scanning mode when the disturbance detecting unit detects an occurrence of disturbance, wherein in the second scanning mode, a first read scan in which a first line not scanned yet is selected for a horizontal scan for reading charge signals from respective light receiving portions corresponding to the first line and a second read scan in which a second line not scanned yet interlaced by a prescribed number of lines from the first line along the sub scanning direction is selected for the horizontal scan for reading charge signals from respective light receiving portions corresponding to the second line are repeated down to a lower end of the sub scanning direction while keeping the prescribed number of lines as an interval between the first line and the second line, wherein the first read scan and the second read scan are repeated down to the lower end of the sub scanning direction again with a line not scanned yet selected from an upper end of the sub scanning direction.

2. The endoscope system according to claim 1, wherein the disturbance detecting unit detects application timing of a high frequency current to a high frequency treatment instrument that is inserted into the subject together with an inserting portion of the endoscope and has a high frequency electrode exposed at a tip thereof, and wherein the controlling unit switches the driving part from the first scanning mode to the second scanning mode based on the application timing of the high frequency current detected by the disturbance detecting unit.

3. The endoscope system according to claim 1, wherein the prescribed number of lines to be interlaced comprises one line interlaced.

4. The endoscope system according to claim 1, further comprising:

a display part that displays image information obtained based on the captured image signal serially transmitted.

5. The endoscope system according to claim 1, wherein the plurality of light receiving portions are arranged in a honeycomb pixel arrangement.

6. The endoscope system according to claim 1, wherein the imaging part comprises a single chip color sensor type imaging part including a color filter that includes a plurality of color segments.

7. The endoscope system according to claim 1, wherein the digital image data serially transmitted has a header region in front of a payload including image information and an ECC (Error Check and Correct) region corresponding to the detection data and an idle region behind the payload.

8. The endoscope system according to claim 1, wherein in the first scanning mode, after a prescribed exposure time, a charge stored is transferred for outputting the charge signals.

9. The endoscope system according to claim 1, wherein in the second scanning mode, the signals are output in a discontinuous order of the lines in the captured image.

10. The endoscope system according to claim 1, wherein the controlling unit switches the driving part to the second scanning mode before supplying a high frequency current to a high frequency treatment instrument.

11. The endoscope system according to claim 1, wherein the controlling unit switches the driving part from the first scanning mode to the second scanning mode after completing a read scan of a whole of the captured image in which the transmission error has been detected.

* * * * *